US012599703B2

(12) United States Patent
Woerly

(10) Patent No.: US 12,599,703 B2
(45) Date of Patent: Apr. 14, 2026

(54) HYBRID HETEROGENEOUS HYDROGEL, MANUFACTURING METHOD AND USE AS AN IN-SITU NON-DEGRADABLE FILLER IMPLANT

(71) Applicant: NEUROBIOMAT, Archamps (FR)

(72) Inventor: Stéphane Woerly, Saint Julien en Genevois (FR)

(73) Assignee: NEUROBIOMAT, Archamps (FR)

( * ) Notice: Subject to any disclaimer, the term of this patent is extended or adjusted under 35 U.S.C. 154(b) by 757 days.

(21) Appl. No.: 17/912,184

(22) PCT Filed: Mar. 17, 2021

(86) PCT No.: PCT/EP2021/056753
§ 371 (c)(1),
(2) Date: Sep. 16, 2022

(87) PCT Pub. No.: WO2021/185881
PCT Pub. Date: Sep. 23, 2021

(65) Prior Publication Data

US 2023/0166005 A1 Jun. 1, 2023

(30) Foreign Application Priority Data

Mar. 17, 2020 (FR) ...................................... 2002619

(51) Int. Cl.

| | |
|---|---|
| ***A61L 27/14*** | (2006.01) |
| ***A61L 27/16*** | (2006.01) |
| ***A61L 27/18*** | (2006.01) |
| ***A61L 27/52*** | (2006.01) |
| ***C08J 7/12*** | (2006.01) |
| ***C08L 33/26*** | (2006.01) |
| ***C08L 101/00*** | (2006.01) |

(52) U.S. Cl.
CPC ............... *A61L 27/52* (2013.01); *A61L 27/14* (2013.01); *A61L 2400/06* (2013.01)

(58) Field of Classification Search
CPC ........ A61L 27/52; A61L 2400/06; C08J 9/24; C08J 9/35; C08J 2300/14; C08J 2300/292; C08L 101/005
See application file for complete search history.

(56) References Cited

U.S. PATENT DOCUMENTS

| | | | | |
|---|---|---|---|---|
| 5,863,551 | A * | 1/1999 | Woerly ..................... | A61P 1/00 523/113 |
| 7,163,545 | B2 | 1/2007 | Yaszemski et al. | |
| 7,569,222 | B2 * | 8/2009 | Woerly ................. | C08F 220/20 424/93.7 |
| 7,846,466 | B2 | 12/2010 | Shea et al. | |
| 8,377,463 | B2 | 2/2013 | Langer et al. | |
| 8,685,434 | B2 | 4/2014 | Langer et al. | |
| 8,815,277 | B2 | 8/2014 | Park et al. | |
| 8,858,966 | B2 | 10/2014 | Langer et al. | |
| 8,877,498 | B2 | 11/2014 | Wegst et al. | |
| 9,440,008 | B2 | 9/2016 | Langer et al. | |
| 9,623,044 | B2 | 4/2017 | Nothias et al. | |
| 9,895,234 | B2 | 2/2018 | Frostell et al. | |
| 10,131,786 | B2 | 11/2018 | Harvey et al. | |
| 2006/0002978 | A1 | 1/2006 | Shea et al. | |
| 2011/0177170 | A1 | 7/2011 | Bryukhovetskiy et al. | |
| 2015/0044259 | A1 | 2/2015 | Desilva | |
| 2015/0166786 | A1 | 6/2015 | Harvey et al. | |
| 2018/0037865 | A1 | 2/2018 | Peduzzi-Nelson et al. | |
| 2025/0041488 | A1 * | 2/2025 | Hamilton ................ | A61L 27/54 |

FOREIGN PATENT DOCUMENTS

| | | | |
|---|---|---|---|
| EP | 2 347 763 | A1 | 7/2011 |
| FR | 2 942 408 | A1 | 8/2010 |
| WO | 98/16266 | A1 | 4/1998 |
| WO | 2010/097524 | A1 | 9/2010 |
| WO | 2011/002249 | A2 | 1/2011 |
| WO | 2013/010087 | A1 | 1/2013 |
| WO | 2013/084137 | A1 | 6/2013 |

(Continued)

OTHER PUBLICATIONS

Machine translation of WO 2010/097524 obtained from the European Patent Office website in May 2025 (Year: 2025).*

(Continued)

*Primary Examiner* — Melissa A Rioja
(74) *Attorney, Agent, or Firm* — Oliff PLC

(57) ABSTRACT

A filler implant includes a support of hybrid heterogeneous hydrogel which is formed by a copolymer including: a dendrimer monomer which is functionalised by an ethylene radical, an acryl amide compound which is selected from an N-substituted methacrylamide and N-substituted acrylamide, a cross-linking agent and a bioactive copolymerisable material. The support is formed by microbeads which have a diameter between 1.5 micrometres and 10 micrometres and it predominantly contains by weight the acrylamide compound. The microbeads are assembled to form aggregates which contain between 5 and 50 microbeads. The aggregates are connected by cross-linking points in order to define a penetrating porous network which defines three-dimensional percolating paths. The penetrating porous network is formed by pores, the majority of the volume of which has a diameter between 10 and 30 micrometres. The support has a viscoelastic nature with a modulus of elasticity between 1 and 200 kPa.

18 Claims, 1 Drawing Sheet

(56) References Cited

FOREIGN PATENT DOCUMENTS

WO 2014/013188 A1 1/2014

OTHER PUBLICATIONS

Gordon et al.; "The potential of electrical stimulation to promote functional recovery after peripheral nerve injury—comparisons between rats and humans;" Acta Neurochir Suppl; 2007; pp. 3-11; vol. 100.
Bõstman et al.; "Adverse Tissue Reactions to Bioabsorbable Fixation Devices;" Clinical Orthopaedics and Related Research; 2009; pp. 216-227; No. 371.
Luo et al.; "Polyethylene glycol immediately repairs neuronal membranes and inhibits free radical production after acute spinal cord injury;" Journal of Neurochemistry; 2002; pp. 471-480; vol. 83.
Nilsson et al.; "The role of complement in biomaterial-induced inflammation;" Molecular Immunology; 2007; pp. 82-94; vol. 44.
Jun. 9, 2021 Search Report issued in International Patent Application No. PCT/EP2021/056753.

* cited by examiner

HYBRID HETEROGENEOUS HYDROGEL, MANUFACTURING METHOD AND USE AS AN IN-SITU NON-DEGRADABLE FILLER IMPLANT

BACKGROUND OF THE INVENTION

The invention relates to a hybrid heterogeneous hydrogel and more particularly to the use thereof as filler implant.

PRIOR ART

An injury to the nerve parenchyma of the spinal cord, whether it be consecutive to a focal trauma, an ischemia, surgical removal of a tumour or a vascular malformation or other causes, results in severing of the nerve fibre connections which interrupts transmission of the nerve impulse commanding the motor functions transmitted by the brain and in return impedes treatment of the sensory functions. This results in complete or partial paralysis.

In the case of a spinal cord injury, the lesion by compression or any other vertebro-medullary impact progresses through neurodegenerative phenomena that develop in centrifugal manner from the epicentre of the lesion and that lead progressively to the chronic stage of the initial injury. In the chronic stage, the lesion is represented by a cystic cavity, isolated and circumscribed by a heterogeneous scar tissue composed of glial cells, fibroblasts, pericytes and meningeal cells, molecules of the extracellular matrix in particular proteoglycans and collagen. This form of healing, in the same way as the intramedullary cavity, is a cause of failure of repair of the nerve fibres of the ingoing and outgoing axonal routes.

Regenerative therapies seek to perform cellular repair of the cystic cavity in the chronic stage of the medullary injury and revascularisation of the damaged area which may represent a large loss of volume with a size varying from 2 to 6 vertebral bodies in height. Regenerative therapies also seek to make the nerve fibres grow through this cystic cavity in order to promote reconnection of the spinal neuronal circuits and re-establish the motor and sensory functions. This strategy takes account of the post-injury plasticity of the nervous system that is able to reform relay circuits between the nerve fibres that are regrowing and intact neurons under the injury level. The strategy used in tissue engineering is to introduce a porous permissive substrate at the level of the lesion (either in the acute stage or in the chronic stage) to act as physical, chemical and mechanical scaffold for the endogenous cell, blood vessel and nerve repair processes leading to histological reconstruction of the nerve tissue.

The scaffolds generally used at experimental level and in clinical tests are represented by a particular class of biomaterials, hydrogels. These are polymer matrices forming a water-saturated, cross-linked macromolecular array. They are used in tissue engineering, in particular where the nervous system is involved.

They are prepared from degradable or bioresorbable polymers to constitute temporally unstable porous structures. These polymers are of natural origin—alginate, agarose, chitosan, collagen, hyaluronic acid, fibrin or peptides, or they are synthetic such as poly caprolactones, poly(hydroxybutyrates), poly(ortho esters), poly(α-hydroxy esters) or polyanhydrides. Degradable and/or bioresorbable hydrogels have thus been proposed to promote nerve regeneration of spinal cord injuries on experimental models or in clinical tests in humans.

Biodegradable hydrogels are those which, once injected into a living organism, degrade by spontaneous chemical hydrolysis for polyanhydrides, poly(ortho esters), and poly (α-hydroxy esters). Thioether-esters degrade in the presence of water and biological polymers (oligopeptides, proteins, or poly-saccharides) degrade due to the action of enzymes or other proteins produced by the cells.

For example U.S. Pat. No. 7,163,545 discloses a poly (lactic-co-glycolic acid) matrix, including guidance channels for axon regeneration in combination with therapeutic agents. U.S. Pat. No. 8,377,463 reports a device formed from poly(lactic-co-glycolic acid) to treat the acute stage of spinal cord injuries that degrades in situ between 30 and 60 days, that is able to be combined with therapeutic agents and/or stem cells. Document US 2018/0037865 describes a complex hydrogel comprising a degradable matrix of hyaluronic acid, collagen, fibrin, chitosan, methylcellulose, polyoxyethylene or a combination thereof, combined with stem cells and therapeutic molecules, which degrade in situ at a variable rate depending on the nature of the polymer. Document US 20060002978 discloses a tubular matrix containing a porous polymer material formed from homo- or copolymers of lactic acid and/or of glycolic acid and/or of poly(caprolactone). The polymer matrix can comprise an aliphatic polyester, a polyanhydride, a polyphosphazine, a polyvinyl alcohol, a polypeptide, or an alginate. U.S. Pat. No. 8,877,498 reports a matrix comprising a hierarchised structure with highly aligned channels and ridges along walls enabling guided regeneration of the nerve fibres, and presenting a composition comprising chitosan, chitin, cellulose, alginate, gelatine, hyaluronic acid, collagen, elastin or a combination thereof. Document WO2014013188 discloses an acetylated chitosan biomaterial in the form of a suspension of microgels or in the form of 2 to 3 $mm^3$ gel to treat spinal cord injuries. Documents US 2015/0166786 A1 and WO2013010087 A1 reveal a hydrogel composed of poly(lactic-co-glycolic acid) or comprising poly(ε-caprolactone) combined with poly(L-lysine) to treat acute injuries of the spinal cord in humans. Document US 2015/0044259 A1 describes a matrix composed of poly-D Lysine and a peptidoglycan to promote growth of nerve fibres. Document EP2347763A1 and document US 2011/0177170 A1 describe a matrix composed of collagen microparticles included in a homogeneous gel composed of peptides, uronic acid and hexosamine for implantation together with a cell graft in the treatment of lesions of the central nervous system, degradation of which takes place between a few weeks and several months. Document WO2013/084137 discloses a degradable implant using calcium sulfate hemihydrate that includes parallel-geometry channels combined with a growth factor for treatment of complete spinal cord injuries in humans.

Biodegradable hydrogels are also proposed such as those presented in document U.S. Pat. No. 8,815,277 or in document WO2011/002249. It is indicated that these systems present the advantage of not being invasive, i.e. they do not require open surgery of the spinal cord in order to be implanted. In general, these systems degrade in situ in two weeks, which is very quick in comparison with a regenerative process.

A hydrogel made from poly(lactic-co-glycolic acid) base is also proposed to repair nerve channels of the spinal cord. This hydrogel degrades in 30 to 60 days in rats, which is a very insufficient time for a successful tissue regeneration if these results are transposed to humans. A comparative study showed that the growth time of isolated axons is longer and the regeneration rate three times slower in humans than in rats (Gordon 2007, The potential of electrical stimulation to promote functional recovery after peripheral nerve injury-comparisons between rats and humans; Acta Neurochir Suppl. 2007; 100:3-11). In the case of the spinal cord, the time is even longer as a large number of nerve fibres have to re-grow to achieve a functional motor recovery. Growth of axons through the chirurgical repair site is slow and asynchronous until the appropriate targets of the segment of spinal cord under the injury level are reached.

These methods to attempt to repair spinal cord injuries have a very limited and imperfect efficiency in regeneration of the central nerve tissue in application to humans as they do not enable the anatomic structures of the damaged medullar segment to be repaired at the same time as achieving functional recovery of the neurological functions.

Once they have been implanted in the organ, the degradable hydrogel matrices degrade by severing of polymer chains at the same time as migration and colonisation of the cells, blood vessels and re-growing nerve fibres take place in the course of the tissue remodelling. In this way, when tissue reconstruction of the spinal cord is carried out, to facilitate the formation of nerve neotissue, the degradable hydrogel matrices present a high degradation rate resulting in a rapid loss of the initial mechanical support properties. For the tissue regeneration to be optimal, i.e. complete in time, it is essential for the hydrogel scaffold to preserve a certain structural integrity in space and time throughout the tissue remodelling process.

It is also apparent that hydrolysis of the ester bonds of the poly(α-hydroxyacid) releases acid compounds which lower the pH when they accumulate in the graft site. Lowering of the pH causes an acceleration of the hydrolysis rate in the centre of the implant as compared with the surface, causing a rapid loss of the initial mechanical properties of the implant and a local reaction to foreign bodies as illustrated in Bostman OM and Pihlajamaki HK (2000) *Adverse tissue reactions to bioabsorbable fixation devices. Clin Orthop Rel Res* 371: 216-227.

Document WO2010/097524 discloses a hybrid heterogeneous hydrogel that is a copolymer derived from the following monomers:

- a dendrimer monomer comprising a central core A, macromolecular dendritic branches of polyoxyethylene with at least one of the dendritic branches functionalised by an acrylate or methacrylate radical,
- an N-substituted methacrylamide or N-substituted acrylamide, and
- a bioactive copolymerisable material chosen from the group consisting of a derivative of a complex sugar, a derivative of a tissue adhesion peptide and a derivative of a polymer conjugate coupled with antibodies directed against lipid derivatives.

OBJECT OF THE INVENTION

One object of the invention consists in remedying these shortcomings, and more particularly in providing an implant made from a hydrogel that presents a lower degradation rate in comparison with hydrogels of the prior art and that is better suited to the mechanical stresses related to cell colonisation.

According to one feature of the invention, a hybrid heterogeneous hydrogel is proposed formed by means of a copolymer derived from at least three of the following monomers:

- a dendrimer monomer functionalised by a single branch provided with an unsaturated ethylene radical,
- an acrylamide compound chosen from an N-substituted methacrylamide and an N-substituted acrylamide, and
- a cross-linking agent.

The hybrid heterogeneous hydrogel is characterised in that the hybrid heterogeneous hydrogel is formed mainly by a plurality of microbeads having a diameter of more than 1.5 microns and less than 10 microns and mainly containing by weight N-substituted methacrylamide and N-substituted acrylamide, the microbeads being assembled to one another to form aggregates containing between 5 and 50 microbeads, the aggregates being joined to one another by cross-linking points to define a through porous array defining three-dimensional percolating paths, the through porous array defining pores the majority of the porous fraction whereof is formed by pores having a diameter comprised between 10 and 30 microns and wherein the hybrid heterogeneous hydrogel has a viscoelastic nature and has a modulus of elasticity comprised between 1 and 200 kPa.

According to one development, the microbeads have a diameter comprised between 2 and 5 microns.

Preferentially, the microbeads comprise at least 90% by weight of the acrylamide compound. Even more preferentially, the microbeads are constituted by the cross-linked acrylamide compound.

In a particular embodiment, the aggregates contain between 10 and 30 microbeads. It is advantageous to provide for the aggregates to be deformable in compression.

Advantageously, the functionalised dendrimer monomer comprises one or more macromolecular dendritic branches of polyoxyethylene, said at least one macromolecular dendritic branch of polyoxyethylene being functionalised by one or more bioactive copolymerisable materials chosen from the group consisting of a derivative of a complex sugar, a derivative of a tissue adhesion peptide and a derivative of a polymer conjugate coupled with antibodies directed against lipid derivatives, said one or more bioactive copolymerisable materials covering the wall of the three-dimensional percolating array.

In preferential manner, the wall of the three-dimensional percolating array is functionalised by means of several different bioactive copolymerisable materials.

In an advantageous configuration, said one or more active molecules are chosen from the group consisting of a derivative of complex sugars, derivatives of a tissue adhesion peptide or of a peptide with an angiogenic activity, derivatives of a peptide stimulating nerve regrowth, derivatives of a peptide stimulating cell proliferation and differentiation, a derivative of a polymer conjugate coupled with antibodies directed against lipid derivatives, and chemokines of the Stromal-derived factor-1 (SDF-1) class.

It is further advantageous to provide for the functionalised dendrimer monomer to comprise a central core A, macromolecular dendritic branches of polyoxyethylene with at least one of the dendritic branches functionalised by a polymerisable acrylate or methacrylate radical.

According to another configuration, the acrylamide compound is N-(2-hydroxypropyl)methacrylamide (HPMA) and the functionalised dendrimer monomer comprises dendritic branches of polyoxyethylene functionalised at their periphery with bioactive agents conferring bioactive properties for tissue regeneration.

Another object of the invention consists in the use of a hybrid heterogeneous hydrogel according to one of the foregoing configurations as filler implant designed to be inserted between the edges of an anatomical defect of an organ or of a tissue.

Preferentially, the hybrid heterogeneous hydrogel is used as filler implant to fill an intra-parenchymal cavity of the central nervous system.

In advantageous manner, the hybrid heterogeneous hydrogel is used as filler implant to correct congenital malformation of the central nervous system or *Spina bifida*.

According to one feature of the invention, a method for fabricating a hybrid heterogeneous hydrogel is proposed that is easy to implement for industrial production, whereby hybrid heterogeneous hydrogels can be produced that are more suitable for formation of a filler implant in particular as far as the physical-chemical specifications are concerned.

The method for fabricating a hybrid heterogeneous hydrogel is remarkable in that it comprises:

- formation of microbeads by phase separation induced by copolymerisation and free radical copolymerisation at a temperature comprised between 45° C. and 55° C. from a reactional mixture comprising at least three of the following monomers:
  - a dendrimer monomer functionalised by a single branch comprising an unsaturated ethylene radical, the other branches being devoid of ethylene radicals,
  - an acrylamide compound chosen from an N-substituted methacrylamide and an N-substituted acrylamide, and
  - at least one bifunctional unsaturated ethylene cross-linking agent comprising two reactive vinyl bonds, and a free radical initiator, the microbeads having a diameter of more than 1.5 microns and less than 10 microns and mainly containing by weight N-substituted methacrylamide and N-substituted acrylamide, the microbeads being assembled to one another to form aggregates containing between 5 and 50 microbeads, the aggregates being joined to one another by cross-linking points to define a hybrid heterogeneous hydrogel delineating a through porous array defining three-dimensional percolating paths, the through porous array defining pores the majority of the porous fraction whereof is formed by pores having a diameter comprised between 10 and 30 microns and wherein the hybrid heterogeneous hydrogel has a viscoelastic nature and has a modulus of elasticity comprised between 1 and 200 kPa; and wherein the reactional mixture is injected into tight cylindrical-shaped, heat-conducting moulds.

In one development, the molar ratio between the functionalised dendrimer monomer and the cross-linking agent is comprised between 0.1 and 0.8. Preferentially, the functionalised dendrimer monomer has a molecular mass comprised between 6,220 g/mol and 23,280 g/mol.

Preferentially, a bioactive copolymerisable material is present in the reactional mixture to form the microbeads, the bioactive copolymerisable material being chosen from the group consisting of a derivative of a complex sugar, a derivative of a tissue adhesion peptide and a derivative of a polymer conjugate coupled with antibodies directed against lipid derivatives.

In an advantageous configuration, the reactional mixture is injected into a metal mould the inner walls of which are covered with polytetrafluoroethylene. The mould is preferentially heated by means of a water bath. Preferentially, polymerisation of the reactional mixture is performed at a first temperature for at least 80 minutes to form the microbeads and the temperature of the mould and of the reactional mixture is then increased by at least 5° C.

In advantageous manner, the method for forming aggregates of microbeads of a hybrid heterogeneous hydrogel according to one of the foregoing configurations is implemented in a method for fabricating a filler implant. The method for fabricating a filler implant comprises formation of aggregates of microbeads of a hybrid heterogeneous hydrogel and assembly of the aggregates to one another by a three-dimensional printing method to form a filler implant.

BRIEF DESCRIPTION OF THE DRAWINGS

Other advantages and features will become more clearly apparent from the following description of particular embodiments and implementation modes of the invention given for non-restrictive example purposes only and represented in the appended drawings, in which.

DESCRIPTION OF THE EMBODIMENTS

Figure 1:
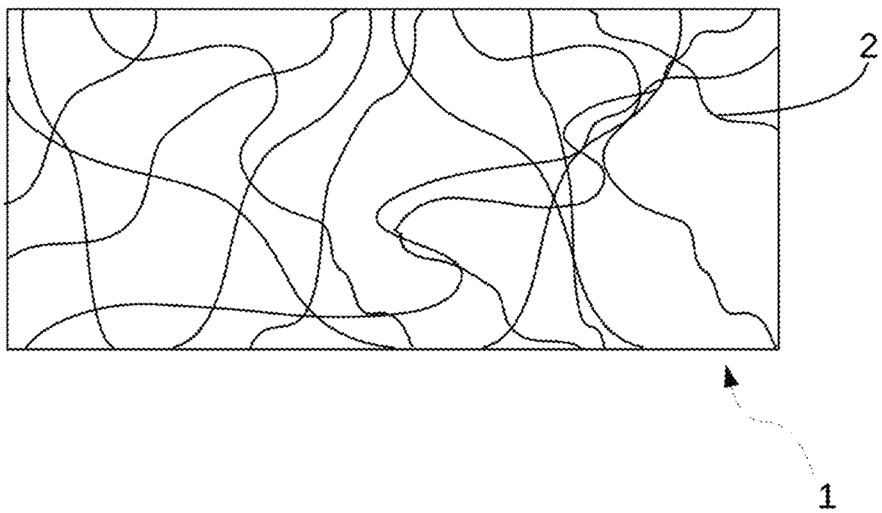
FIG. 1 schematically illustrates an implant provided with a hybrid heterogeneous hydrogel defining three-dimensional through channels.

An implant made from a hydrogel base is designed to be implanted in a cavity representing a volumetric tissue loss, for example a medullary cavity. If the degradation rate ($V_d$) of the hydrogel is faster than the cell regeneration rate ($V_r$), there is rapidly no longer any support for the tissue reconstruction. The tissue reconstruction will be limited to the periphery of the implantation area and the cell regeneration process will be incomplete. In addition, biodegradation of the scaffolds of polymers implanted in the medullary injury lead to physical separation between the body of the implant and the spinal cord tissue. The space separating the implant from the tissue is filled with cerebrospinal liquid and prevents the hydrogel from being integrated in the nerve tissue. This also prevents the axons in the course of regeneration from reaching the body of the scaffold formed by the implant.

Generation of acid degradation products may lead to an acute inflammatory response. Other degradation products may have toxic effects at cell level and interfere with homeostasis of an organ. These degradation products are generated over time until the polymer support is completely destroyed. The degradation products can be transported by systemic circulation to accumulate in sequential manner in target organs the long-term consequences of which may be damaging for the organ.

For the regeneration process to be optimal and complete, the degradation rate of the polymer array of the implant has to match the tissue repair rate so that the decrease of the total volume of the gel with the increasing volume of the cellular bioburden in progression remains constant so as not to impose mechanical compression stresses on the interfaces with the host organ. Such stresses would cause lesions by ischemic compression. Although it is possible to control the degradation rate of a polymer hydrogel in vitro under strictly controlled experimental conditions, it is impossible to control the degradation rate of the hydrogel matrix in vivo and to monitor the degradation rate of the polymer matrix with respect to the cellular bioburden rate in vivo. It is therefore impossible to use a biodegradable implant efficiently in a regeneration process.

In general, the cell regeneration process and the degradation process of the implant start from the interface in contact with the spinal cord and extend towards the inside of the cavity. Furthermore, the centre of the hydrogel matrix does not degrade completely and remains in the form of oligomer chains that have lost their structure and their function of growth substrate. The implant is no longer usable as it does not provide any mechanical support and it ends up by impeding the reconstruction.

Degradation of the matrix can further lead to a dissociation of the connections that exist between the cells that migrated into the structure of the hydrogel. These connections are essential in formation and cohesion of a functional tissue.

The use of a degradable polymer hydrogel as implant in tissue engineering for optimal repair of a loss of volume of tissue in particular of the nervous system therefore has to take into account both the evolution of the mechanical behaviour of the hydrogel matrix in the course of use for the latter to preserve its structural integrity until the new biological tissue has been formed and also its actual in-vivo degradation rate. This is not possible since, as it degrades, the matrix progressively loses its architectural topography and therefore its mechanical properties which are defined by its initial architecture. The structural integrity of the implant cannot be maintained over time. The structural integrity of the implant is however an essential characteristic to sustain formation of the tissue reconstruction throughout the tissue reconstruction.

After an injury, the nerve fibres have a natural ability to regenerate either by elongation or by collateral sprouting. This ability is greatly reduced if the ends of the regenerating fibres, the growth cones, do not find any substrate to adhere to and lengthen.

However, if the matrix is degraded, the substrate via which the growth cones can progress in the axon regeneration process cannot be continuous. It is therefore advantageous to use an implant made from a hydrogel having a degradation rate $V_d$ that is lower than or equal to the regeneration rate $V_r$ of the tissue.

It is particularly advantageous to use a hybrid heterogeneous hydrogel that is non-degradable, i.e. that has a lower degradation rate than the regeneration rate. Preferentially, what is meant by non-degradable hybrid heterogeneous hydrogel is a polymer composition that is not subject to in-situ degradation by chemical or enzymatic hydrolysis reaction or cleavage by photolysis, under physiological conditions representative of the human body. For example, the chemical degradation is low or zero over a reference period at least equal to one or two years.

The hybrid heterogeneous hydrogel degradability study is advantageously carried out at 40° C. in an acid solution having a pH equal to 1 and in an alkali solution having a pH equal to 14. A piece of hydrogel is placed in each of these solutions and each solution is kept at 40° C., for example by means of a hot plate. The solution is stirred. The hybrid heterogeneous hydrogel sample and the solution are observed regularly. For example, it is observed that after one week, a non-degradable hybrid heterogeneous hydrogel has not changed aspect and the solution has remained clear. No floating residue of the sample is observed in the solution. Nor is any loss of mass of the hydrogel observed.

The acid solution is advantageously a hydrochloric acid solution at 0.1 mol/L. The alkali solution is advantageously a soda solution at 1 mol/L.

The hybrid heterogeneous hydrogel is also analysed by high-performance liquid chromatography. A mixture containing 25% volume of methanol and 75% of water is preferentially used as eluent. The flowrate of the eluent is advantageously 1 mL/min. The column used can be of Nova-Pack C18 150 mm 3.9 mm reversed-phase type. Analysis of the chromatograms enables degradation of the hydrogel to be detected by searching for its constituents.

With a non-degradable hybrid heterogeneous hydrogel, analysis of the chromatograms shows very few new peaks in the course of time. For example, the chromatograms were analysed in order to monitor the main constituents of a hydrogel according to the invention, for example a hydrogel containing HPMA (N-(2-Hydroxypropyl) methacrylamide). The high-performance liquid chromatography analyses do not show any degradation of the HPMA-base hydrogel. These observations are corroborated by “in vivo” tests where the HPMA-base gel is implanted in a spinal cord. Analysis of the cerebrospinal liquid by electrophoresis does not show any degradation product of oligomer type in the cerebrospinal liquid. This absence of degradation product shows an absence of degradation of the hydrogel.

It is also advantageous to have a hydrogel that is not bioresorbable and that is compressible. Such a hydrogel can be used as filler implant and can be inserted between the edges of an anatomical defect of an organ for example of the nervous system and in particular a post-traumatic intramedullary cystic cavity.

However, as the implant degrades little or not at all, the volume of the implant must not impede cell reconstruction. It is particularly advantageous to form a filler implant that comprises a scaffold made from porous hybrid heterogeneous hydrogel with through pores allowing cellular regeneration within the implant. As illustrated in FIG. 1, it is particularly advantageous for hybrid heterogeneous hydrogel 1 to have a porous structure the pores of which communicate with one another to create a percolating array 2 in the three dimensions of the volume of the gel. The through array formed by the pores enables the cells to migrate and proliferate up to the core of the hydrogel, to join up and survive due to transport and diffusion of the nutrients necessary for the cellular metabolism.

As the hydrogel is non-degradable, the pore arrays do not induce an increased degradation of the hydrogel with stagnation of toxic or irritant molecules in the pores.

The implant is a porous structure with open pores passing through the implant to define percolating paths in the three dimensions of the hydrogel. The open pores enhance cellular and vascular colonisation from the tissue through to the core of the implant as well as circulation of biological fluids, cell growth factors, cellular repair factors and physiological nutrients through the implant. Flow of the different fluids through the implant promotes vascularisation of the tissue generated in the implant. The implant forms a three-dimensional support matrix the pores through of which guide the growth of cells, nerve fibres and blood vessels. The cell growth is of better quality in contact with the implant than without the implant. The implant must be formed solely by the hydrogel.

In preferential manner, the porous fraction of the hydrogel forming the implant is greater than 85%, more preferentially at least equal to 90% and even more preferentially at least equal to 92% in volume. The porous fraction can be calculated with a mercury porosimetry technique.

It is preferable to have a hybrid heterogeneous hydrogel most of the porous fraction of which is formed by pores having a diameter comprised between 10 and 30 microns. Preferentially, at least 60% of the porous fraction is formed by pores having a diameter comprised between 10 and 30 microns. In other words, at least 60% of the porous volume is constituted by pores having a diameter comprised between 10 and 30 microns.

It is also advantageous to have a hybrid heterogeneous hydrogel the pores of which having a diameter comprised between 30 and 300 microns represent a lager fraction than the pores having a diameter of less than 10 microns. In preferential manner, the fraction of pores having a diameter comprised between 30 and 300 microns is greater than 20%, even more preferentially greater than 30%. The fraction of pores having a diameter comprised between 30 and 300 microns is particularly advantageous for housing biological objects of large size such as multicellular tissues. Advantageously, the fraction of pores having a diameter of less than 10 microns is less than 15%, even more preferentially less than 10%. It is further advantageous for the hybrid heterogeneous hydrogel to comprise less than 2% in volume of pores having a size of less than 1 micron in the through porous array.

Such a distribution in the dimensions of the pores ensures that the biological compounds pass through the implant covering the whole dimensional spectrum of the biological compounds of living tissue. This results in use of the implant as tissular equivalent of the organ to be repaired being easier to implement.

The pores of the implant are compatible with the circulation of chemokines secreted by the inflammatory cells. The configuration of the implant enables infiltration of glial cells, mesenchymal cells, stem/progenitor cells associated with leptomeninges secreting SDF-1 factor and stem/progenitor cells associated with the epithelium of the central channel having a neuronal differentiation potential, infiltration of the blood vessels and growth of regenerating nerve fibres.

It is also advantageous to form a hybrid heterogeneous hydrogel from a material that presents the property of changing the configuration of its porous array progressively with the cell colonisation or the quantity of cellular bioburden. The hybrid heterogeneous hydrogel can deform under the stress applied by the cell colonisation and/or cellular bioburden. The implant deforms progressively under the pressure exerted by the cell tissue as regeneration takes place. The hydrogel has to be able to deform with the mechanical stresses of the cellular bioburden enabling a structure with percolating channels to be kept.

It is particularly advantageous to form a filler implant that comprises a scaffold made from porous hybrid heterogeneous hydrogel which is deformable in viscoelastic manner with a sufficiently low degradation rate for the hydrogel to be considered as a non-degradable hybrid heterogeneous hydrogel. The volume occupied by the porous implant will change as regeneration takes place to partly adapt to match the regeneration rate around and in the hydrogel.

When cell and nerve regeneration takes place, the macromolecular skeleton of the hybrid heterogeneous hydrogel deforms with a constant or substantially constant volume. During the cellular accumulation in the implant and during the expansion of the neotissue that is forming, the polymer array deforms under the mechanical pressure exerted by the cellular accumulation. The structure of the implant is made from a material that has a modulus of elasticity comprised between 1 and 200 KPa in order to adapt to the stress applied by the cellular bioburden. The value of the modulus of elasticity can be measured at 50% of its deformation before severing.

As the cellular bioburden progressively increases, the implant deforms according to the mechanical stresses introduced by the cellular bioburden in the implant. The implant deforms elastically and then viscoelastically so as not to impede the cell growth in particular in the through channels. In spite of its deformation, the implant keeps a three-dimensional percolating array that stretches to ensure complete tissue regeneration. Once the tissue has been reconstructed, the residual polymer array of the implant acts as intercellular support matrix stabilising the neotissue formed by exerting a mechanical strain.

The surface of the implant has a large roughness which makes for a good adhesion with the host tissue by increasing the contact surface between the implant and the cells of the tissue in contact, which will promote adhesion between the two environments. The open pores at the surface of the implant that are joined to the percolating array promote cellular and vascular colonisation through to the core of the implant from the tissue in contact at the same time as circulation of the biological fluids, cell growth factors and physiological nutrients necessary for the cell.

The use of a hybrid heterogeneous hydrogel able to form a matrix having elastic properties and a porous structure suitable for treatment and repair of an organ and/or tissue regeneration and in particular its use as implantable biomaterial is known from the document FR 2942408. It was observed that such a material has a lower degradation rate than the regeneration rate of a cell tissue.

It is particularly advantageous to improve the hybrid heterogeneous hydrogel known from the document FR 2942408 to form a non-degradable scaffold with a porous structure that specifically defines percolating channels in the three dimensions and has a viscoelastic behaviour with a modulus of elasticity comprised between 1 and 200 kPa.

It is advantageous to use a hybrid heterogeneous hydrogel that is a copolymer derived from at least three monomers—a dendrimer monomer functionalised by an ethylene radical, an acrylamide monomer and a cross-linking agent. In a particular configuration, the hybrid heterogeneous hydrogel comprises a bioactive copolymerisable material. In another particular configuration, the hybrid heterogeneous hydrogel does not contain any bioactive copolymerisable material. Bioactivation can be performed subsequently on the formed hydrogel.

The bioactive copolymerisable material is chosen from the group comprising derivatives of a complex sugar, of a tissue adhesion peptide and of a polymer conjugate coupled with antibodies directed against lipid derivatives. Preferentially, the bioactive copolymerisable material is a methacryloyl or methacrylamide derivative of a complex sugar, of a tissue adhesion peptide and of a polymer conjugate coupled with antibodies directed against lipid derivatives, The bioactive copolymerisable material can be a preferably methacryloyl or methacrylamide derivative of a complex sugar chosen for example from glucosamine, N-acetylglucosamine, N-diglycidyl-glucosamine, N-acetylgalactosamine, N-acetylneuraminic acid (sialic acid) and polysialic acid.

The bioactive copolymerisable material can be a preferably methacryloyl or methacrylamide derivative of a tissue adhesion peptide chosen from tissue adhesion oligopeptides containing amino acid sequences such as Arg-Gly-Asp, Ile-Lys-Val-Ala-Val, Ala-His-Ala-Val-Ser-Glu, Tyr-Ile-Gly-Ser-Arg, oligopeptide derivatives of tissue differentiation molecules, for example bone morphogenetic proteins or proteins of the SDF-1 (Stromal cell derived factor-1) family, a chemokine that has the ability to mobilise and attract endogenous stem cells expressing the CXCR4 receptor and that has the ability to stimulate growth of axons when tissue regeneration takes place.

The bioactive copolymerisable material can be a preferably methacryloyl or methacrylamide derivative of a polymer conjugate coupled with antibodies against myelin and its lipid derivatives associated with axons.

The acrylamide monomer is advantageously an N-substituted methacrylamide or N-substituted acrylamide. The value of the modulus of elasticity is partly defined by the cross-linking density of the hydrogel, i.e. by the number of covalent bonds between the macromolecular chains formed from the acrylamide monomer, preferably by monitoring the number of covalent bonds between the macromolecular HPMA chains.

The N-substituted methacrylamide is preferably chosen from the group consisting of N-monoalkylmethacrylamide, N,N-dialkylmethacrylamide, N-hydroxyalkylmethacrylamide, preferentially N-(2-hydroxypropyl)methacrylamide (HPMA), N-alkyl, N-hydroxyalkylmethacrylamide, and N,N-dihydroxyalkylmethacrylamide.

The N-substituted acrylamide is preferably chosen from the group consisting of N-monoalkylacrylamide, N-hydroxyalkylacrylamide, N,N-dialkylacrylamide, N-alkyl, N-hydroxyalkylacrylamide and N,N-dihydroxyalkylacrylamide.

The dendrimer monomer preferentially comprises a central core A and macromolecular dendritic branches of polyethylene oxide (PEO). Only one of the dendritic branches is functionalised, advantageously in terminal position, by an ethylene radical. The ethylene radical is unsaturated in order to react with a monomer comprising at least one reactive vinyl double bond. The other dendritic branches are preferably terminated by a hydroxyl function and are devoid of ethylene radicals. They can also be functionalised before copolymerisation by other functions such as ester or amide functions. The ethylene radical is advantageously an acrylate or methacrylate radical. The star architecture of the dendrimer enables a multifunctional variable geometry to be introduced in the hydrogel to respond in specific manner to the multiple interactions envisaged with other materials. The indication by which only one of the branches is functionalised corresponds to a statistical result indicating that, on average, the dendrimer monomer is functionalised by a single branch provided with an unsaturated ethylene radical.

The functional hydroxyl groups in the hybrid heterogeneous hydrogel can be modified by attaching entities, for example bioactive agents such as polypeptides, active principles, ligands, polymerisable groups or oligo-saccharides.

According to a particular embodiment, the central core A is a group chosen from a carbosilane, a polycarbosilane, a star-architecture polycarbosilane, or a group according to the following formula (1):

$$-(CH_2)_n-Si-(CH_2)_n- \qquad (1)$$

where n is an integer comprised between 1 and 20, preferably equal to 6.

According to a variant, the central core A is a poly (divinylbenzene).

According to a preferential embodiment, the dendrimer monomer complies with the following formula (2):

$$(CH_2{=}CR-CO-O-(CH_2CH_2O)_{Z'})_Y\text{-}A\text{-}(O-(CH_2CH_2O)_Z-H)_X \qquad (2)$$

in which:

R is H or $CH_3$,

X and Y are integers comprised between 1 and 100 and the sum X+Y is a multiple of 4, and Z and Z' are identical or different and comprised between 1 and 100, and A being preferably a carbosilane, a polycarbosilane, a star-architecture polycarbosilane, or a group according to formula (1).

According to another preferential embodiment, the dendrimer monomer complies with the following formula (3):

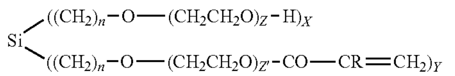

(3)

in which:

R is H or $CH_3$, n being an integer comprised between 1 and 20, preferably equal to 6, Z and Z' are identical or different and comprised between 1 and 100, X is equal to 1, 2 or 3 and, Y complies with the formula Y=4-X.

Advantageously, the dendrimer monomer is functionalised by a methyl methacrylate radical and has four dendritic branches of PEO and a silane central core A with a hexanol bridge i.e. having a structure of formula (3) with R=$CH_3$, n=6, X=3, Y=1, and Z=Z'. For reasons of clarity, this dendrimer monomer will be identified by the notation Si-PEO4-MMA.

The mechanical and chemical properties of the hydrogel can also be adjusted by grafting functions with specific properties such as hydrophilic, hydrophobic and/or tensioactive properties on the free hydroxyl terminations of the dendritic branches. The hydroxyl function can be easily functionalised on account of the nucleophile nature of its oxygen atom. This function is known to be easily activated, for example by basic treatment. The intrinsic properties of the hybrid heterogeneous hydrogel can also be modified by varying the number of dendrimer monomers incorporated in the hydrogel skeleton and the nature of the central core A. The number of dendritic branches conditions the solubility of the macromolecule in water and organic solvents.

The hybrid heterogeneous hydrogel is mainly formed or is constituted by a plurality of microbeads assembled to one another to define the through porous array. The microbeads present a spherical or substantially spherical shape and mainly a diameter of more than 1.5 microns and less than 10 microns. In preferential manner, the microbeads mainly present a diameter comprised between 2 and 5 microns to better modulate the deformation of the channels according to the stress applied by the cellular bioburden.

In order to better control the conformation of the three-dimensional percolating array, it is preferable to agglomerate the hydrogel microbeads in the form of aggregates comprising at least 5 microbeads and less than 50 microbeads and preferentially at least 10 microbeads. In advantageous manner, the microbeads agglomerate with one another to form aggregates in groups of 10 to 30 microbeads. It is also particularly advantageous for the hydrogel microbeads to agglomerate with one another in a configuration called "bunch of grapes" which facilitates formation of an efficient porous array while ensuring a good deformability of the scaffold. It is preferable for the aggregates to be formed by microbeads having a diameter comprised between 5 and 10 microns. The aggregates preferentially form the primary array of the hydrogel matrix. The aggregates are fixed to one another by attachment points allowing one aggregate to shift with respect to another. In a bunch of grapes conformation, the cross-section is increasing from one end to the other and the cross-section is substantially circular perpendicularly to the length of the aggregate. The bunch of grapes conformation is more advantageous than the linear configuration to facilitate the interactions between the cells and implant thereby facilitating the formation of a multicellular tissue structure and/or growth of the nerve fibres. The bunch of grapes conformation also improves the adhesion.

In an aggregate, the microbeads are fixed to one another by deformable cross-linking points to allow the microbeads to shift with respect to one another and adapt the conformation of the hybrid heterogeneous hydrogel scaffold according to the mechanical stresses applied. The aggregate can be compressed. The polymer chains deform between the cross-linking points by stretching. The cross-linking points shift away from one another resulting in an increase of the porous fraction of the hydrogel. When cell and nerve regeneration take place, the total porous volume of the implant increases at constant volume with an anisotropic configuration.

The microbead aggregates are constructed in mobile manner with respect to one another so as to allow contraction of the microbead aggregates in response to the capillary pressure exerted by the migrating cells in contact with the surface of the microbeads. The microbead aggregates are configured so that contraction of the latter has the effect of expanding the porous array and of increasing the porous volume available for expansion of the forming tissue.

The aggregates are fixed to one another to form a porous array comprising mesoporous and macroporous areas. The multiple pores defined by the aggregates are connected to one another to form a percolating array that presents a certain tortuosity and that passes through the hydrogel in its initial configuration. At microscopic level, the percolating array allows infiltration of the cells, blood vessels and nerve fibres through the hydrogel in the three dimensions of space when the tissue bioreconstruction process takes place. In parallel, the microbeads define micropores with a size smaller than 20 nm, preferably a size that varies within the 1.5 to 11 nanometre range with a mean diameter of 6 nanometres. These micropores are closed and non-communicating. The micropores form craters at the surface of the microbeads, which gives the hydrogel microbeads a honeycomb surface. These micropores create surface and contribute to increasing the internal specific surface of the macromolecular hydrogel array formed from these hydrogel microbeads. This increase of the macromolecular array surface and the surface topography of the microbeads promote interactions with the cell membranes in particular focal adhesions of the migrating cells.

Preferentially, the percolating array defines a large internal specific surface, at least equal to 25 $m^2/g$, advantageously at least 50 $m^2/g$.

In the prior art, on account of the degradation of the hydrogel matrix, it was observed that the cellular bioburden mass increases with time and partly fills the volume lost by the hydrogel matrix. It is also apparent that the degradation rate of the hydrogel is higher than the cell colonisation rate which complicates distribution of the bioburden in the volume initially occupied by the implant. On the contrary, with a non-degradable hybrid hydrogel that is porous and visco-elastically deformable, the bioburden increases per volume unit of the tissue defect taking advantage of compression and deformation of the hydrogel. The cell colonisation is better mastered. The deformable macro-molecular array is modified over time with the growth of the cells that organise, migrate and differentiate in autonomous manner to form a functional neotissue.

It is particularly advantageous to form an implant with a cross-linking density that is inhomogeneous. The difference of cross-linking degree can be defined by means of the fabrication method used. It is preferential to use a copolymerisation of the hydrogel by means of a method implementing phase separation of the reactional mixture, and it is also advantageous to implement a copolymerisation method wherein the phase separation originates from polymerisation induced via thermal means. It is particularly advantageous to control the phase separation by performing the cross-linking in a defined temperature range. For example, good results were obtained with a phase separation comprised between 40° C. and 60° C. A scaffold with better performances was obtained with a cross-linking comprised between 45° C. and 55° C. A scaffold with even better performances was obtained with a cross-linking comprised between 49° C. and 51° C. The use of such a temperature range enables the dimensions of the microbeads to be better defined.

It is also advantageous to limit the polymerisation rate to ensure formation of a hydrogel associating good mechanical performances and the through channels. In preferential manner, the cross-linking time is more than 6 hours or even more than 12 hours to form an implant.

It is particularly advantageous to fabricate an implant in which the agglomerates are regions of the hydrogel array where the cross-linking density is high. The hydrogel is formed by aggregates strongly cross-linked to one another by weakly cross-linked areas. The strongly cross-linked aggregates form mechanical support areas which can shift with respect to one another by means of the weakly cross-linked areas.

The cross-linking points between the aggregates are formed by covalent bonds, i.e. chemical bonds that can be considered as non-degradable, which makes for a good mechanical strength between the aggregates. It is advantageous to provide for the aggregates to be distributed in statistical manner in the hydrogel volume defining areas with a high polymeric chain concentration and areas with a low polymeric chain concentration and forming cavities containing free water.

The mean distance between two cross-linking points in the strongly cross-linked areas is less than 20% of the mean distance between two cross-linking points in the weakly cross-linked areas, preferably less than 10% of the mean distance between two cross-linking points in the weakly cross-linked areas.

It is preferable for the proportion of the strongly cross-linked area to represent at least 60% of the total volume of the hydrogel intrusion. It is also advantageous for the proportion of the strongly cross-linked area to represent less than 80% of the total volume of the hydrogel intrusion.

The surface of the implant is not flat. It presents defects for example protuberances originating from assembly of the microbeads.

It is particularly advantageous to fabricate a hybrid heterogeneous hydrogel in which the microbeads comprise at least 90% by weight or even at least 95% by weight or are constituted by the acrylamide compound, for example N-substituted methacrylamide or N-substituted acrylamide, to give the microbeads elastic properties ensuring deformation of the implant with the cellular burden. In particular manner, the microbeads mainly or exclusively made from acrylamide compound have a diameter comprised between 1.5 and 10 microns, preferably between 2 and 5 microns.

In preferential manner, the microbeads mainly contain HPMA weight by weight, preferably strongly cross-linked HPMA. In advantageous manner, a strongly cross-linked microbead has a cross-linking rate of more than 1 mol % of cross-linker. The use of such a cross-linking rate ensures the existence of a sufficient number of transverse chemical bonds between the linear polymer chains per volume unit of hydrogel. This configuration gives the hydrogel a sufficient cohesion of the polymeric arrays, for example the HPMA, for a swell ratio at equilibrium of 96% of the final mass (g of water/g dry matter). In the present case, this ratio is preferentially 0.95 mol %. More weakly cross-linked material (for example HPMA) can be used to form the bonds between the microbeads and to define the microbead aggregates.

It is particularly advantageous to provide for the through channels of the implant to be delineated by microbeads the functionalised dendrimer monomer of which comprises one or more macromolecular dendritic branches of polyoxyethylene. The macromolecular dendritic branches of polyoxyethylene are functionalised by one or more active molecules, for example one of the bioactive copolymerisable materials described in the above. It is then possible to functionalise the surface of the percolating array to facilitate the cell reconstruction within the implant.

The active molecule is chosen from the group consisting of a derivative of complex sugars, derivatives of tissue adhesion peptide or of peptide with an angiogenic activity, derivatives of a peptide stimulating nerve regrowth, derivatives of a peptide stimulating cell proliferation and differentiation, a derivative of a polymer conjugate coupled with antibodies directed against lipid derivatives, and chemokines of the Stromal-derived factor-1 (SDF-1) class.

It is also advantageous to provide for the use of microbeads in which the acrylamide compound is N-(2-hydroxypropyl) methacrylamide (HPMA) and the dendrimer monomer functionalised by an ethylene radical comprises polyoxyethylene dendrimers functionalised at their periphery with bioactive agents providing bioactive properties for tissue regeneration.

In the same way as for document FR 2942408, a hybrid heterogeneous hydrogel can be fabricated by means of a radical copolymerisation. The preferential polymerisation method is performed in an polar organic medium and advantageously bi-organic polar medium, for example an acetone/DMSO mixture.

In advantageous manner, in addition to the radical copolymerisation, copolymerisation is associated with a polymerisation-induced phase separation (PIPS). In this way, the initially homogeneous solution of monomers and polar solvents separates during copolymerisation to form the microbeads. Advantageously, the molar ratio between the functionalised dendrimer monomer and the cross-linking agent is comprised between 0.1 and 0.8, for example PEO-MMA/MbisAA ratio comprised between 0.1 and 0.8. With this ratio value, the phase separation defines balls of twine, called coils, forming the microbeads. In the 45°-55° C. temperature range, it is easier to obtain mainly coils made from acrylamide compound with a diameter comprised between 1.5 and 10 microns. This ratio value also allows the formation of a three-dimensional percolating array. It is even easier to control the number of coils generated and the size distribution of the coils by choosing a functionalised dendrimer monomer with a molecular mass comprised between 6,220 g/mol and 23,280 g/mol. In this particular range, when the molar mass of the functionalised dendrimer monomer increases, the number of coils increases and the size distribution decreases.

Figure 2:
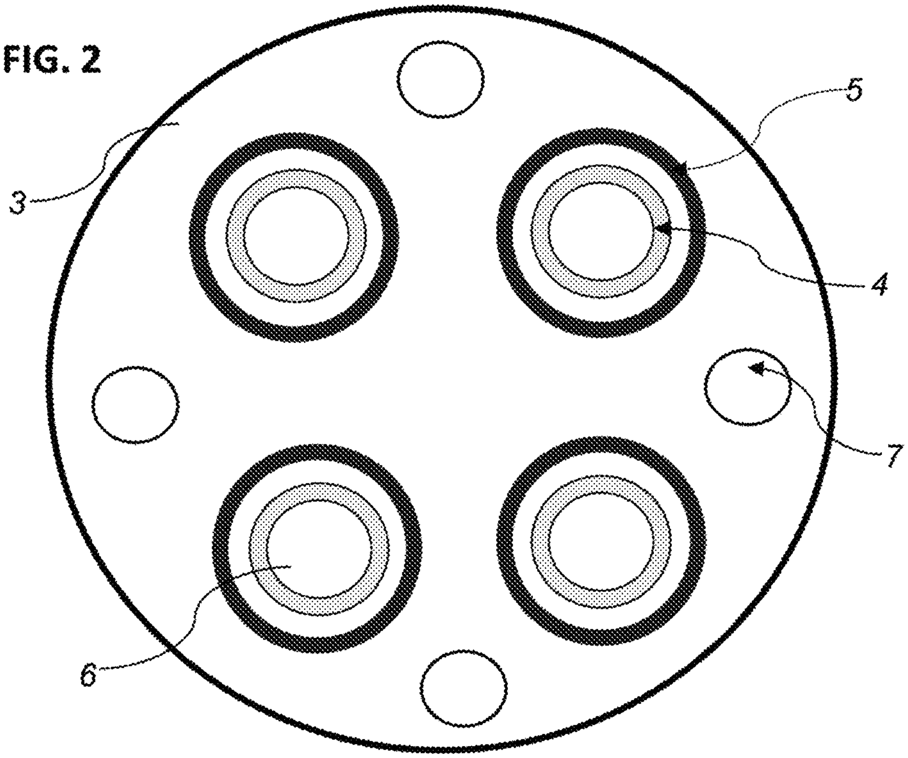
FIG. 2 illustrates a metallic body defining four cylindrical wells the walls of which are covered by a surface made from PTFE.

The method for forming the hybrid heterogeneous hydrogel comprises a first phase of reaction of the reactional mixture forming insoluble nuclei constituted by coil-shaped polymer chains. As illustrated in FIG. 2, the reactional mixture is injected into tight cylindrical-shaped, heat-conducting moulds 3 with walls 4 made from PTFE in contact with the reactional mixture. The reactional mixture can have undergone degassing with argon. The mould 3 includes several wells 6 and apertures 7 as well as an associated seal 5, as explained further below.

The microbeads are associated to form the aggregates and the aggregates are linked to one another to form the hybrid heterogeneous hydrogel designed to form the filler implant.

It is also possible to provide for supply of microbead aggregates and assembly of the aggregates to one another by a three-dimensional printing method to form the filler implant. The form of the implant is directly defined by the three-dimensional printing equipment.

Copolymerisation is performed by means of a cross-linking agent. The cross-linking agent can be an acrylamide such as methylene bisacrylamide (MbisAA), precursors of the latter or divinyl compounds such as divinylbenzene (DVB). The free radical polymerisation initiator is selected from known initiators such as azobisisobutyronitrile (AIBN) or benzoyl peroxide.

The cross-linking agent is preferentially methylene bisacrylamide (MbisAA) which has two vinyl groups. Methylene bisacrylamide allows a greater reactivity in comparison with N-(2-hydroxypropyl)methacrylamide (HPMA) which only has one vinyl group. This enables a faster incorporation of methylene bisacrylamide in the growing chains which form nuclei before forming the microbeads.

It is particularly advantageous to use a polyoxyethylene hydrogel as polyoxyethylene has shown a neuroprotective effect on neuronal membranes and reduces the post-lesion oxidative stress (Luo et al. *Polyethylene glycol immediately repairs neuronal membranes and inhibits free radical production after spinal cord injury. J. Neurochem.* 83, 471, 2002). It is preferable to use a hydrogel formed from one or more polymers of branched star structure with polyoxyethylene branches enhancing the biocompatibility of the hydrogel in particular by preventing non-specific absorption of blood proteins, thereby modulating the local inflammatory response by reducing activation of the complement by cleavage of the C3 protein into peptides responsible for recruitment of phagocyte cells (Nilsson, B., et al. *The role of complement in biomaterial-induced inflammation. Mol Immunol* 44, 82, 2007).

These branched molecules can be modified with functional groups of the class of peptides, bioactive sugars, and chemokines by bioconjugation in terminal position of the polyoxyethylene branches. It is particularly advantageous to form a hydrogel material that has a porous structure formed in a scaffold comprising a structure composed of N-(2-Hydroxypropyl) methacrylamide and a branched structure formed by branched polyoxyethylene polymer vectors of functional groups. The functional groups are preferentially short peptides such as oligopeptides interacting with the integrin receptors of the cells, for example but not limited to the following sequences, Arg-Gly-Asp, (RGD), Arg-Gly-Asp-Ser (RGDS), Ile-Lys-Val-Ala-Val (IKVAV). Other functional groups can be oligomers conjugate with one or more sialic acids, for example sialyllactose (Neu5Ac-α2,3-Gal-β1,4-Glc), and also sulfate oligosaccharides such as HNK1 ($SO_4$-3-GlcAβ1-4Galβ1-4GlcNac-R) or fucosylated oligosaccharides, for example Fuc α(1-2)Gal. Bioactive agents can also be chosen from the growth factors that stimulate axon regeneration including but not limited to BDNF ("Brain Derived Neurotrophic Factors"), IGF-1 ("Insulin-like Growth Factor"), NT-3 ("Neurotrophin"), GDNF ("Glial Derived Neurotrophic Factor"); or that stimulate proliferation of neuronal precursors such as FGF ("Fibroblast Growth Factors"), and EGF ("Epidermal Growth Factor), PDGF ("Platelet-derived Growth Factor"), VEGF ("Vascular Endothelial Growth Factor"), PIGF ("Placental Growth Factor"), NGF ("Nerve Growth Factor") and TGF ("Transforming Growth Factor") can be conjugated with the POE.

Bioactive agents that stimulate mobilisation of precursor stem cells such as SDF-1 (Stromal-derived factor-1) chemokines that have the ability to attract endogenous stem cells expressing the receptor CXCR4 and to stimulate axon growth when tissue regeneration takes place, G-CSF (granulocyte colony-stimulating factor), GM-CSF (granulocyte-macrophage colony-stimulating factor) or SCF(Stem cell factor) cytokines and interleukin (IT-8).

One embodiment of the hydrogel is advantageously fabricated in an inert atmosphere and comprises a hydrogel combining N-(2-hydroxypropyl) methacrylamide with the cross-linking agent N,N'-Methylenebisacrylamide or N,N'-Methylenebismethacrylamide comprising two vinyl groups in a molar ratio of 100:1 for 30.4% by weight of the total weight of the reactional mixture; a bi-organic polar solvent acetone/DMSO (93/7 v/v).

The reactional mixture is degassed with argon and injected into tight cylindrical-shaped, heat-conducting moulds with walls made from PTFE in contact with the reactional mixture. In advantageous manner, the initial reactional mixture is placed in a metal mould preferably made from stainless steel the inner walls of which are covered by polytetrafluoroethylene (PTFE). The reactional mixture is purged with an inert gas directly inside the mould. Preferentially, the mould has a circular cross-section with a height at least twice the size of the diameter. The use of a metal mould makes the latter easier to use with a water bath that fixes the temperature of the mould and of the reactional mixture during polymerisation. This configuration enables the dimensions of the microbeads and of the pores to be better controlled.

A radical polymerisation reaction is performed preferentially in the presence of the azobisisobutyronitrile initiator at 50° C. It was observed that it is particularly advantageous to increase the temperature of the mould and of the reactional mixture by at least 5° C., preferably by 10° C. or more, in the course of polymerisation. It is advantageous for the temperature increase to be less than 20° C. It is also advantageous for the maximum temperature of the polymerisation to be lower than 70° C. and even more preferentially lower than 65° C. in order not to degrade the xerogel, i.e. the hydrogel before it is saturated with water. This temperature increase enables a more homogeneous distribution of the polymer chains in the hydrogel and a better efficiency to be obtained. In preferential manner, the temperature increase is performed after formation of the microbeads or of a majority of the microbeads. The temperature increase can take place at least after 80 minutes of polymerisation, even more preferentially after 90 minutes of polymerisation. The polymerisation can be performed with a first temperature plateau used to form the microbeads, for example a temperature plateau comprised between 45° C. and 55° C., preferably equal to 50° C. The temperature plateau is then followed by a second plateau or possibly by a temperature gradient or another form of annealing to a temperature at least 5° C. higher than the temperature of the plateau. The use of two different temperature ranges enables a better control of the dimensions of the microbeads and a better control of the dimensions of the aggregates to be achieved. Preferably, during the first temperature plateau, polymerisation is performed until the oligomer concentration reaches a threshold value enabling longer chains to be formed by condensation of the oligomers. Condensation of the oligomers results in the appearance of at least two phases having different densities. It is advantageous to perform a phase separation by modifying the polymerisation temperature.

In order to detect that the threshold oligomer concentration has been reached, it is advantageous to monitor the absorbance signal of the reaction. For example, an absorbance signal is monitored by absorption spectrometry (optical density) in the ultraviolet-visible range. Detection of a sufficient quantity of long chains obtained by condensation of the oligomers can correspond to a threshold absorbance value or a progression rate of the absorbance that reaches a threshold value. Once the threshold value has been detected, the long chains are known to be in sufficient quantity. A second polymerisation step is performed at higher temperature, preferentially with a second plateau that is at least 5° C. higher than the previous plateau. The second plateau enables copolymerisation to be achieved by accelerating nucleation and allowing polymerisation to continue. Cross-linked oligomer coils are formed forming the microbeads. The microbeads aggregate randomly and the cross-linking points are formed. During the second polymerisation phase at higher temperature, the absorbance value decreases. As an alternative, the second plateau is replaced by a temperature gradient or a more complex temperature progression having a minimum temperature that is at least 5° C. higher than the temperature of the first plateau.

During polymerisation, as illustrated in FIG. 2, it is preferable to close mould 3 tightly, for example by means of a polytetrafluoroethylene cover advantageously associated with a seal 5. Use of the cover limits evaporation of the solvents from the reactional mixture and enables a better reproducibility to be achieved.

In preferential manner, the dimensions of the mould are chosen such that the hydrogel formed from the mould presents a diameter equal to 175 mm and a height equal to 400 mm for a hydrated gel. It is also advantageous to use one and the same metal part defining several moulds in the form of several wells 6. Mould 3 can comprise apertures 7 designed to collaborate with screws to close off well 6 as illustrated in FIG. 2.

At the end of polymerisation, the xerogel is in dry or anhydrous form and is taken out of the mould. It is particularly advantageous to cover the inner walls of the mould with polytetrafluoroethylene as this makes the hydrogel in dry form easier to take out thereby avoiding damaging the latter. The xerogel present in the mould is friable which makes it a fragile material that is easily damaged when it is extracted from the vial used in prior art methods.

Washing of the xerogel in ethanol/pyrogen-free water is performed enabling it to reach a swell ratio at equilibrium of 96%. As an alternative, the ethanol is replaced by methanol. In advantageous manner, the xerogel is transferred to a first recipient that is in the form of a perforated basket, the basket advantageously being made from polytetrafluoroethylene. In preferential manner, the first basket is installed in a second basket containing a liquid. The liquid can be water, ethanol or methanol or a mixture of water with ethanol or methanol. The liquid of the second recipient passes through the holes of the first recipient to clean the xerogel.

It is particularly advantageous for the second recipient to be opaque to visible radiation. The second recipient can be made from polycarbonate.

The xerogel installed in the first recipient is subjected to a washing cycle that advantageously comprises application of several successive washing baths. The water content is increasing in the different baths in order to clean the xerogel and saturate it with water to form the hydrogel.

The hydrogel is advantageously cross-linked with methylenebisacrylamide in a ratio equal or substantially also equal to 1 mol % which gives the hydrogel advantageous physical characteristics as filler implant.

For use of the latter in surgery as filler implant to be handled under aseptic conditions, the sterility of the product has to be ensured. The gel is advantageously placed in a cylindrical container made from high-grade PTFE, a material that does not interact with the chemical nature of the gel, and filled with pyrogen-free injectable-grade water. The PTFE container with the gel is sterilised by autoclaving at 121° C. for 30 minutes and the container is reclosed tightly with a screw-fastened cover so that the gel remains saturated with water and sterile. This container is placed in a second container made from polystyrene with a “snap safe cap” which is open onto a sterile operating field. The PTFE container can thus be handled in sterile manner. The polystyrene second container can present a height equal to 54 mm, an inner diameter equal to 34 mm and a thickness equal to 1.5 mm.

The hybrid heterogeneous hydrogel is advantageously used in a filling strategy in order to modify the natural healing phenomena by performing filling by a regeneration phenomenon in the presence of a viscoelastic matrix that has the property of changing the configuration of its porous geometric space and the configuration of its polymer array. The elasticity effects of the hydrogel provide the advantage of being able to modify the mechanical elastic properties of the substrate and reconstitute a mechanical environment close to that of the in-vivo cells. Such a hydrogel is able to receive and guide fluxes of cells, nerve fibres and blood vessels.

The hybrid heterogeneous hydrogel defines an elastically deformable and continuous porous medium that is non-degradable and non-bioresorbable with a geometry that adapts to the cellular, vascular and nerve regeneration kinetics. Once it has been implanted in an incised area, the hydrogel matrix anchors onto the spinal cord enabling the hydrogel matrix to follow the movements of the spinal cord caused by the movements of the spinal column and by the beating of the arteries that irrigate this organ and to therefore remain anchored to the graft site. The implant forms a support structure due to its open porous structure that enables the cell flux to migrate into the polymer matrix following the percolating paths of the porous array.

In a particular embodiment, the hybrid heterogeneous hydrogel forms an implant in a graft cavity, for example an intramedullary cavity. The cavity can be formed by dissection and elimination of non-living scar tissues from an inner edge of the lesion. The edges of the cavity are formed by healthy nerve tissue. In an advantageous embodiment, provision of the cavity is followed by draining of the cerebrospinal liquid. This enables a “de novo” lesion to be created that is equivalent to an acute lesion which reactivates the inflammatory processes of endogenous cellular repair (mobilisation of stem cells, sprouting of nerve ends, angiogenesis). The implantation method also comprises a filling step of the post-traumatic cavity with injection of the hydrogel into the intramedullary cavity. The hydrogel can be cut to adjust to the shape and geometry of the cavity.

It is particularly advantageous to partially dehydrate the hydrogel before inserting the latter into the cavity. After it has been installed in the cavity, the hydrogel swells subsequent to coming into contact with the fluids circulating in the cavity until the hydrogel implant is in contact with the whole of the surface of the cavity so that it forms an integral (100%) interface with the white matter of the intact peri-lesional nerve tissue. The hydrogel is able to absorb a large quantity of water and swells in the presence of water and of biological liquids containing water. It is advantageous for the hydrogel to contain at least 80% in volume of water at equilibrium. It is advantageous to provide the hydrogel with a water content lower than or equal to 75% volume. Preferentially, the implant is dehydrated so as to have a reduction of its volume comprised between 10% and 30%. It is also advantageous to perform dehydration of the surfaces of the cavity, for example the parenchymal surfaces. It is preferable to dehydrate the walls with an ophthalmic sponge. The implant is then inserted in the cavity, preferably an intraparenchymal cavity, and is then rehydrated to reach at least 95% of its initial volume, preferably 100% of its initial volume. Hydration of the implant to reach its initial volume can be performed in less than one minute. In preferential manner, the volume of the implant with a swell ratio equal to 100% represents between 80% and 100% of the volume of the cavity to be filled. Once the implant has been rehydrated, the porous surfaces of the implant come into contact with the surfaces of the cavity thereby enhancing the adhesion. It is advantageous to have a gradient in the dehydration rate with a central portion that is more hydrated than the peripheral portion. A larger dehydration at the surface improves the quality of the subsequent contact with the wall of the cavity.

To enhance the adhesion of the implant with the walls of the cavity, it is preferable to dehydrate and then hydrate the walls designed to come into contact. It is also preferable to have an implant that comes in the form of a plurality of bunches of grape formed by microbeads. The conformation of the implant with the above-mentioned microbeads defines a surface roughness with spikes and protuberances. It is advantageous to have a roughness less than or equal to 30 micrometres, preferably less than or equal to 15 micrometres and even more advantageously less than or equal to 5 micrometres. It is also advantageous for the roughness to be greater than or equal to 0.1 micrometre. Such a roughness range promotes circulation of the interstitial fluids between the surface of the hydrogel and the parenchyma. This surface texture results from the bunch structure of the hydrogel microbeads. Adhesion is also enhanced by the surface pores on the protuberances on a nanometric scale.

It is particularly advantageous to cover the surface of the hydrogel with living peri-lesional white matter comprising the ingoing, outgoing and associative nerve fibres. The implant is particularly designed to closely follow the geometry of the surfaces of the cavity. These steps lead to the anatomic reconstitution of the spinal cord at the level of its traumatic area. It is particularly advantageous to cover the implant with living peri-lesional white matter comprising the ingoing, outgoing and associative nerve fibres to take advantage of the bioadhesive properties of the implant with the biological tissue.

In order to improve the quality of the reconstruction, it is advantageous to have an implant that possesses bioadhesive properties or improved bioadhesive properties. By adapting the surface properties of the implant, the adhesion between the implant and the biological tissue is thereby improved.

When the implant has improved bioadhesive properties, it is able to be inserted in the cavity and a quality cell reconstruction be obtained without using surgical suturing with the biological tissue.

It is particularly advantageous for the implant to actively stimulate hemostasis and more particularly the primary phase of hemostasis. It is also advantageous for the implant to actively stimulate platelet aggregation. In this way, the implant induces blood coagulation which makes a good tissue reconstruction easier to achieve. This particular implant configuration enables micro-bleeding to be controlled as close as possible to the interface between the implant and cavity thereby preventing formation of a degraded interface between the implant and tissue. In-vitro blood coagulation and platelet aggregation tests and also in-vivo tests highlighted the satisfactory control of hemostasis by the implant.

The invention claimed is:

1. A hybrid heterogeneous hydrogel prepared from a copolymer derived from a reaction mixture comprising the following monomers:

a dendrimer monomer comprising a plurality of branches and in which only a single branch is functionalized with an unsaturated ethylene radical, an acrylamide compound chosen from an N-substituted methacrylamide and an N-substituted acrylamide, and a cross-linking agent, wherein the hybrid heterogeneous hydrogel is formed by a plurality of microbeads having a diameter of more than 1.5 microns and less than 10 microns, wherein the microbeads are assembled to define a through porous array defining three-dimensional percolating paths, wherein the through porous array further defines pores, a majority thereof having a diameter of between 10 and 30 microns, and a fraction of pores in the through porous array having a diameter between 30 and 300 microns is more than 20%, wherein the microbeads contain closed non-communicating micropores having a size that is smaller than 20 nm, the microbeads are assembled to one another to form aggregates containing between 5 and 50 microbeads, wherein the aggregates have weakly cross-linked areas connecting the aggregates to each other which allow shifting of the aggregates in relation to each other, and wherein the hybrid heterogeneous hydrogel has a viscoelastic nature and has a modulus of elasticity between 1 and 200 kPa.

2. The hybrid heterogeneous hydrogel according to claim 1 wherein a fraction of pores in the through porous array having a diameter between 10 and 30 microns is more than 60%.

3. The hybrid heterogeneous hydrogel according to claim 1 wherein the microbeads comprise at least 90% by weight of polymerized acrylamide compound.

4. The hybrid heterogeneous hydrogel according to claim 1 wherein the aggregates contain between 10 and 30 microbeads.

5. The hybrid heterogeneous hydrogel according to claim 1 wherein the aggregates have a conformation resembling a bunch of grapes, each aggregate having an increasing cross-section from one end to the other end along a length of the aggregate with a cross-section that is substantially circular in a sectional plane that is perpendicular to the length of the aggregate.

6. The hybrid heterogeneous hydrogel according to claim 1 wherein the dendrimer monomer comprises one macromolecular dendritic branch of polyoxyethylene, the macromolecular dendritic branch of polyoxyethylene being functionalized by one or more bioactive copolymerizable materials chosen from the group consisting of a derivative of a complex sugar, a derivative of a tissue adhesion peptide and a derivative of a polymer conjugate coupled with antibodies against lipid derivatives, the one or more bioactive copolymerizable materials covering a wall of the three-dimensional percolating paths of the through porous array.

7. The hybrid heterogeneous hydrogel according to claim 6 wherein the wall of the three-dimensional percolating paths is functionalised by means of several different bioactive copolymerizable materials.

8. The hybrid heterogeneous hydrogel according to claim 1 wherein the dendrimer monomer comprises one macromolecular dendritic branch of polyoxyethylene, the macromolecular dendritic branch of polyoxyethylene being functionalized by one or more bioactive molecules, wherein the one or more bioactive molecules are chosen from the group consisting of a derivative of complex sugars, derivatives of a tissue adhesion peptide or of a peptide with an angiogenic activity, derivatives of a peptide stimulating nerve re-growth, derivatives of a peptide stimulating cell proliferation and differentiation, a derivative of a polymer conjugate coupled with antibodies against lipid derivatives, and chemokines of the Stromal-derived factor-1 (SDF-1) class.

9. The hybrid heterogeneous hydrogel according to claim 1 wherein the dendrimer monomer comprises a central core A, and said plurality of branches are polyoxyethylene branches and said unsaturated ethylene radical is an acrylate or methacrylate radical.

10. The hybrid heterogeneous hydrogel according to claim 1 wherein the acrylamide compound is N-(2-hydroxypropyl) methacrylamide (HPMA) and said plurality of branches are polyoxyethylene branches and said plurality of branches which do not correspond to the single branch functionalized with an unsaturated ethylene radical are functionalized at their periphery with bioactive agents conferring bioactive properties for tissue regeneration.

11. A method comprising applying the hybrid heterogeneous hydrogel according to claim 1 as a permanent filler implant.

12. A method for fabricating a hybrid heterogeneous hydrogel comprising:

forming microbeads by phase separation induced by copolymerization at a temperature between 45° C. and 55° C. from a reaction mixture comprising the following compounds:

a dendrimer monomer having a plurality of branches and in which only a single branch is functionalized with an unsaturated ethylene radical, the other branches being devoid of ethylene radicals, an acrylamide compound chosen from an N-substituted methacrylamide and N-substituted acrylamide, and at least one bifunctional unsaturated ethylene cross-linking agent comprising two reactive vinyl bonds, and a free radical initiator, the microbeads defining closed non-communicating micropores having a size that is smaller than 20 nm, the microbeads having a diameter of more than 1.5 microns and less than 10 microns, the microbeads being assembled to one another to form aggregates between 5 and 50 microbeads, the aggregates being joined to one another by cross-linking points to define a hybrid heterogeneous hydrogel having a through porous array defining three-dimensional percolating paths and pores, a majority of said pores having a diameter between 10 and 30 microns and a fraction of pores having a diameter between 30 and 300 microns is more than 20% and wherein the hybrid heterogeneous hydrogel has a viscoelastic nature and has a modulus of elasticity between 1 and 200 kPa;

wherein copolymerization is performed with a first temperature plateau followed by a second plateau or a temperature gradient to form the microbeads, the temperature of the first plateau being between 45° C. and 55° C. and the second plateau or the temperature gradient having temperatures at least 5° C. higher than the temperature of the first plateau and wherein the reaction mixture is injected into cylindrical-shaped, heat-conducting molds.

13. The method for fabricating a hybrid heterogeneous hydrogel according to claim 12 wherein the molar ratio between the dendrimer monomer and the at least one bifunctional unsaturated ethylene cross-linking agent is between 0.1 and 0.8.

14. The method for fabricating a hybrid heterogeneous hydrogel according to the claim 13 wherein the dendrimer monomer has a molecular mass between 6,220 g/mol and 23,280 g/mol.

15. The method for fabricating a hybrid heterogeneous hydrogel according to claim 12 wherein a bioactive copolymerizable material is present in the reaction mixture forming the microbeads, the bioactive copolymerizable material being chosen from the group consisting of a derivative of a complex sugar, a derivative of a tissue adhesion peptide and a derivative of a polymer conjugate coupled with antibodies against lipid derivatives.

16. The method for fabricating a hybrid heterogeneous hydrogel according to claim 12 wherein the reaction mixture is injected into molds having inner walls covered by polytetrafluoroethylene.

17. The method for fabricating a hybrid heterogeneous hydrogel according to claim 12 comprising copolymerizing the reaction mixture at a first temperature for at least 80 minutes to form the microbeads followed by a temperature increase of the molds and of the reaction mixture by at least 5° C.

18. A method for fabricating a filler implant comprising fabricating a hybrid heterogenous hydrogel according to the method of claim 12 and further comprising assembling of the aggregates to one another by a three-dimensional printing method to form a filler implant.

* * * * *